United States Patent [19]

Rowe et al.

[11] Patent Number: 4,559,401

[45] Date of Patent: Dec. 17, 1985

[54] PROCESS FOR PREPARING CHROMOPHORE-SUBSTITUTED VINYL-HALOMETHYL-S-TRIAZINES

[75] Inventors: William Rowe, Califon; Thomas Dooley, Teaneck; Ajay Shah, Elizabeth, all of N.J.

[73] Assignee: Polychrome Corporation, Yonkers, N.Y.

[21] Appl. No.: 617,042

[22] Filed: Jun. 4, 1984

[51] Int. Cl.$^4$ .............................................. C07D 251/24
[52] U.S. Cl. .................................... 544/216; 544/211; 544/212
[58] Field of Search ......................... 544/216, 211, 212

[56] References Cited

U.S. PATENT DOCUMENTS 3,987,037 10/1976 Bonham et al. ..................... 544/216

*Primary Examiner*—John M. Ford

[57] ABSTRACT

An improved method for the preparation of chromophore-substituted vinyl-halomethyl-s-triazines especially 2-(p-methoxystyryl)-4,6-bis-(trichloromethyl)-s-triazine. In the known preparation of these compounds, a two step procedure is utilized wherein an intermediate reaction product has to be isolated. This step of separating the intermediate is eliminated in the present process by dissolving the crude reaction product obtained in the first step in toluene, removing excess hydrogen chloride gas and catalysts by purging the reaction product solution with an inert gas, and then reacting p-anisaldehyde with the toluene solution of the reaction product mixture using piperidinium acetate catalyst to obtain 2-(p-methoxystyryl)-4,6-bis-(trichloromethyl)-s-triazine.

As a further improvement of the art the Knoevenagel-type condensation is run until no further water is evolved. At this point the product formed is isolated by filtration and a like amount of catalyst as a second charge is added. Again, the reaction is carried out until no further water is evolved and further product is isolated by filtration.

5 Claims, No Drawings

PROCESS FOR PREPARING CHROMOPHORE-SUBSTITUTED VINYL-HALOMETHYL-S-TRIAZINES

FIELD OF THE INVENTION

The present invention relates to an improved method for preparing chromophore-substituted vinyl-halomethyl-s-triazines, and more particularly to 2-(p-methoxy styryl)-4,6-bis(trichloromethyl)-s-triazine, which at times is referred to as Triazine D.

BACKGROUND OF THE INVENTION

In U.S. Pat. No. 3,987,037 as well as in U.S. Pat. No. 3,954,475 a two step method is disclosed for preparing chromophore substituted vinyl-halomethyl-s-triazines having the following formula:

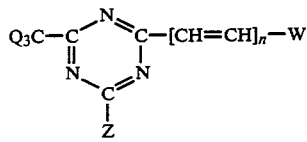

where Q is bromine or chlorine; Z is $-CQ_3$, $-NH_2$, $-NHR_1$, $NR_2$, or $-OR$ where R is phenyl or lower alkyl, preferably an alkyl group having no more than 6 carbon atoms; n is an integer from 1 to 3, and W is optionally substituted aromatic or heterocyclic nucleus.

Although 2-(p methoxy styryl)-4,6 bis(trichloromethyl)-s-triazine is one of the especially preferred s-triazines, some of other useful compounds include:
2-styryl-4,6-bis(trichloromethyl)-s-triazine;
2(4-chlorostyryl)-4,6-bis(trichloromethyl)-s-triazine;
2(3,4-dimethoxystyryl)-4,6-bis(trichloromethyl)-s-triazine;
2(2,4-dimethoxystyryl)-4,6-bis(trichloromethyl)-s-triazine;
2[(4-dimethylamino)styryl]-4,6-bis(trichloromethyl)-s-triazine;
2(4-pentoxystyryl)-4,6-bis(trichloromethyl)-s-triazine; and
2(4-methoxystyryl)-4-amino-6-trichloromethyl-s-triazine, In general, an example of the known preparation involved initially making 2,4-bis(trichloromethyl)-6-methyl-s-triazine. Separating this intermediate compound from the resulting reaction procedure, and then condensing it with p-anisaldehyde. More particularly, the initial step involves the preparation of the methyl-halomethyl-s-triazine intermediate by co-trimerization of organic nitriles and haloacetonitriles in accordance with the teachings of Wakabayashi et al., Bulletin of the Chemical Society of Japan, 42, 2924–30 (1969).

The intermediate compound is 2,4-bis-(trichloromethyl)-6-methyl-s-triazine. In practicing the known process in large scale or for commercial operations the isolation of this intermediate compound has proven to be quite difficult, since the crude reaction product must be melted by heating to 110° C. and then subsequently added to water to isolate very sticky material. Consequently, large excess of water and much time is required in order to isolate and purify the intermediate compound.

It would be desirable to have available a process that could be readily adaptable for commercial and continuous operations which avoided the disadvantages of the known two step procedure described in U.S. Pat. No. 3,987,037. It would be particularly advantageous to have a process which did not require the time consuming and cumbersome step of separating the intermediate compound from the crude reaction product obtained in the initial step of the overall procedure. Previous descriptions of the art for the preparation of the 2-(p-methoxystyryl)-4,6-bis(trichloromethyl)-s-triazine on scale-up gave very inferior yields. The innovation herein described overcame that limitation.

OBJECTS OF THE INVENTION

One object of the present invention is to provide an improved method for preparing chromophore-substituted vinylhalomethyl-s-triazines which avoid the problems associated with the known procedure.

Another object of the present invention is to provide a simplified process involving maximum yields for preparing 2-(p-methoxy styryl)-4,6-bis(trichloromethyl)-s-triazine, i.e., Triazine D, which is adaptable for large scale, commercial, continuous operations.

SUMMARY OF THE INVENTION

In accordance with the present invention it now has been found that an improved method for producing chromophore-substituted vinyl-halomethyl-s-triazine can be achieved by eliminating the step of isolating the intermediate product from the crude reaction product obtained by reaction of an organic nitrile with a haloacetonitrile in the presence of a Friedel-Craft catalyst such as aluminum bromide, aluminum chloride. This separation step is avoided by dissolving the crude reaction product mixture in toluene, which is one of the solvents that can be used in the second step of this process, and by removing excess hydrogen chloride gas and catalyst from the toluene solution of the reaction product mixture by purging it with an inert gas. The inert gas can be nitrogen, argon, and the like, as well as mixtures thereof. The resulting toluene solution containing the intermediate product, e.g. 2,4-bis-(trichloromethyl)-6-methyl-s-triazine is then reacted in the second step with an aldehyde such as p-anisaldehyde in the presence of a catalyst such as piperidinium acetate. This condensation reaction of methyl-halomethyl-s-triazines with aldehydes takes place under conditions typical of the known Knoenenagel reaction. For most purposes, it has been found advantageous to carry out the reaction in the presence of a solvent such as toluene, pyridine, benzene, ethylacetate, methanol, ethanol, and the like. It is especially preferred to use toluene both for the dissolution of the initial reaction product mixture as well as in the second step which involves the condensation of the aldehyde with the s-triazine compound. This condensation procedure is also described in U.S. Pat. No. 3,987,037. Attention being especially directed to the disclosure commencing in the paragraph bridging columns 4 and 5.

As further disclosed in U.S. Pat. No. 3,987,037, the condensation of methyl-halomethyl-s-triazines with aldehydes and aldehyde derivatives is generally carried out in the presence of preferred catalysts which are salts such as piperidinium acetate. In order to obtain a maximum yield the reaction is run until the evolution of water ceases. Then the reaction is cooled filtered and product isolated. To the toluene filtrate is added a like charge at catalyst and again the reaction is run until no water is evolved. Again product is isolated. This procedure leads to increased yields.

DETAILED DESCRIPTION OF THE INVENTION

In general, the chromophore-substituted vinylhalomethyl-s-triazine products are prepared in accordance with the present invention by modification of the known two step procedure. This will be described below with respect to the preparation of 2-(p-methoxystyryl)-4,6-bis(trichloromethyl)-s-triazine.

The initial step involves reacting acetonitrile with trichloroacetonitrile in the presence of a powdered, anhydrous Friedel-Craft catalyst such as aluminum bromide. The resulting reaction mixture is cooled to minus 5° C. and that temperature is maintained throughout the reaction. Hydrogen chloride gas is then bubbled into the mixture over a period which may range from 4 to 7 hours in order to saturate the mixture. The resulting reaction product mixture is a thick, white slurry. After standing for awhile, the slurry turns into a white solid mass. The toluene is then added to the solid and the mixture is gradually heated to a temperature within the range of about 70° to 100° C. over a period of from about 2 to 3 hours. The toluene solution thus obtained is then agitated by being purged with a nitrogen gas for a time period until substantially all of the hydrogen chloride gas is removed from the system by this inert gas purge. The purged toluene solution is then cooled to room temperature and admixed with water. The solution is then filtered to remove insolubles which are believed to be the Friedel-Crafts catalyst decomposition products as well as polymeric by-products. The water layer is then separated from the toluene layer, and the latter is dried over sodium sulfate to remove substantially all of the water from the solution which is designated as the intermediate solution.

The intermediate solution is then admixed with a toluene suspension of piperidine acetate. The latter is prepared in a separate step which will be described below. After stirring the catalyst and intermediate solutions, p-anisaldehyde is added, and the resulting admixture is heated to reflux under a nitrogen sparge. The reaction temperature will generally range from about 100° to 110° C. and heating will be continued for a time period of at least 5 hours, and preferably from 5 to 7 hours. The water evolved from the heated admixture is recovered and separated. The resulting reaction product is then cooled to room temperature and product filtered off. The filtrate is admixed with a second portion of a toluene suspension of the catalyst, i.e. piperidine acetate. After stirring the resulting mixture the reaction product mixture is again heated to reflux and water collected overhead. The reaction will be continued for another 5 to 7 hours or at least until no water is collected overhead.

The final reaction product mixture is cooled to room temperature, filtered, and washed with petroleum ether and then with ethanol. The solid material is the desired product, i.e. Triazine D. If desired, it can be further purified by being recrystallized from a mixture of ethyl acetate and ethanol.

The present invention will be more fully understood by reference to the following illustrative embodiment.

EXAMPLE

In a 12 liter reaction flask, kept in an ice-salt bath, and equipped with a stirrer, condenser, thermometer, gas inlet and outlet tubes, gas traps, etc. were mixed 3719 g. pre-cooled trichloroacetonitrile and 644 g. of pre-cooled acetonitrile, 45 g. of powdered anhydrous aluminum bromide with stirring. The temperature was brought down to −5° C., and the mixture was maintained at that temperature throughout the reaction.

Hydrogen chloride gas was bubbled into the mixture for about 5 hours until saturation was attained and a thick white slurry developed. Approximately 3 lbs of the hydrogen chloride gas was utilized. After the resulting reaction product mixture was allowed to reach room temperature gradually, standing overnight, the reaction product mixture became a solid, white mass.

Approximately 4 kilograms of toluene was added to the solid, white reaction product. The resulting mixture is gradually heated to 80° C. over a 3 hour period. At that temperature the toluene solution was purged with nitrogen gas under agitation to remove the hydrogen chloride gas from the system. The toluene solution was cooled to room temperature, admixed with 500 ml of deionized water under stirring for 4 hours. Insolubles were filtered from the toluene solution followed by separation of the water layer therefrom. The toluene layer was dried over anhydrous sodium sulfate.

The toluene solution is admixed with a catalyst comprising a toluene suspension of piperidine acetate. The catalyst suspension was prepared in a 22 liter reaction flask by adding thereto 1500 g toluene and 314 g piperidine at 25° C. with agitation and over a 30 minute period portions of 222 g glacial acetic acid. Strong exotherms up to 50° C. were observed as a white suspension formed. This suspension was stirred for at least 5 hours while protecting it from moisture, and left overnight or it may be prepared a few days prior to condensation of the toluene reaction mixture with p-anisaldehyde.

To the admixture of the catalyst and the toluene reaction mixture solution, 1780 g of p-anisaldehyde were added with stirring. The resulting mixture was heated to reflux under a nitrogen sparge. The reaction was carried out for 7 hours at the reflux temperature of about 110° C. Water is collected overhead in two Dean's traps. The reaction may be stopped once water evolution ceases. The mixture is then cooled to room temperature, and the precipitated crude product is filtered off.

A second catalyst addition (the preparation of which is described above) was next added to the filtrate and then the temperature was raised to the reflux temperature of 110° C. Again, the reaction was carried out for 7 hours or until water evolution ceased. A total of approximately 210 ml of water was collected.

The reaction mixture was then cooled and filtered to recover the solid product, which was crude Triazine D. The Triazine D was purified by being washed twice with petroleum ether and once with cold ethanol. The weight of the product was 3300–3500 g (crude yield equaled about 63–68%).

If further purification of the product is desired, it can be carried out by using a solvent mixture of ethyl acetate:ethyl alcohol in a ratio of solvent mixture to crude of 7.5:1 (w/w) and with the ethyl acetate to ethyl alcohol ratio of 2.4:1.

The purified, yellow material weighed about 3000 g. which was a yield of 58% (based on trichloroacetonitrile). The melting point was 190°–192° C., extinction value (the intensity of absorption times 0.1 concentration in grams per liter) was 77.5 at 377 nm in acetone.

Although certain aspects of the present invention have been set forth above, it will be understood that the improved method of this invention is subject to variations and modifications without departing from the basic concepts and features.

What is claimed is:

1. In a process for preparing 2-(p-methoxystyryl)4,6-bis(trichloromethyl)-s-triazine by reaction of 2,4-bis(trichloromethyl)-6-methyl-s-triazine with p-anisaldehyde in toluene in the presence of a condensation catalyst; the improvement which comprises using in said reaction a toluene solution of the 2,4-bis(trichloromethyl)-6-methyl-s-triazine obtained by dissolving in toluene a crude reaction product mixture of the 2,4-bis(trichloromethyl)-6-methyl-s-triazine produced by reaction of an admixture of trichloroacetonitrile and acetonitrile with hydrogen chloride in the presence of a Friedel-Crafts catalyst, passing an inert gas through said toluene solution to remove excess hydrogen chloride, adding water to said toluene, separating insoluble Friedel-Craft catalysts therefrom, and recovering said toluene solution of 2,4-bis(trichloromethyl)-6-methyl-s-triazine.

2. In the process of claim 1 wherein the Friedel-Craft catalyst is an aluminum halide.

3. In the process of claim 2 wherein the aluminum halide is aluminum bromide.

4. In the process of claim 1 wherein said inert gas is nitrogen.

5. In the process of claim 1 wherein the condensation catalyst is piperidinium acetate.

* * * * *